United States Patent [19]

Berthold

[11] 4,247,479
[45] Jan. 27, 1981

[54] PROCESS FOR THE MANUFACTURE OF AROMATIC AMINES FROM α, β-UNSATURATED CYCLOALIPHATIC KETOXIMES

[75] Inventor: Rüdiger Berthold, Bad Soden am Taunus, Fed. Rep. of Germany

[73] Assignee: Hoechst Aktiengesellschaft, Frankfurt, Fed. Rep. of Germany

[21] Appl. No.: 45,833

[22] Filed: Jun. 5, 1979

Related U.S. Application Data

[63] Continuation-in-part of Ser. No. 856,739, Dec. 1, 1979, abandoned.

[30] Foreign Application Priority Data

Dec. 3, 1976 [DE] Fed. Rep. of Germany ....... 2654852
Nov. 30, 1977 [CH] Switzerland ........................ 14664/77
Dec. 2, 1977 [JP] Japan ................................. 52-144096
Dec. 2, 1977 [GB] United Kingdom ............... 50341/77
Dec. 5, 1977 [FR] France ............................. 7736520 77

[51] Int. Cl.³ ............................................. C07C 85/11
[52] U.S. Cl. ..................................... 564/436; 564/86; 564/163; 564/307; 564/441; 564/442; 564/443
[58] Field of Search ................... 260/578, 571, 556 A, 260/556 AR, 558 R, 561 R

[56] References Cited

PUBLICATIONS

Adcock et al., "JACS", vol. 89, pp. 386–390 (1967).

Primary Examiner—John Doll
Attorney, Agent, or Firm—Curtis, Morris & Stafford

[57] ABSTRACT

Aromatic amines are obtained in high yield and purity by treating the corresponding cyclohex-2-en-1-on-oxime hydrochlorides with the at least threefold molar amount of acetic anhydride.

9 Claims, No Drawings

PROCESS FOR THE MANUFACTURE OF AROMATIC AMINES FROM α, β-UNSATURATED CYCLOALIPHATIC KETOXIMES

This is a continuation-in-part of my prior application Ser. No. 856,739, filed Dec. 1, 1977, now abandoned.

In the aromatisation named after Semmler and Wolff, aromatic amines are obtained from α,β-unsaturated aliphatic ketoximes, formally by elimination of water (Houben-Weyl: Methoden der org. Chemie [Methods of Organic Chemistry], volume 10/4 (1968) 265, Krauch-Kunz, Reaktionen der organischen Chemie [Reactions in Organic Chemistry], 5th edition, 585 and Org. React. 11, 1).

The earlier literature references do not quote any yields, but it is reported that by-products appear, sometimes to a considerable extent.

Preparatively satisfactory yields are obtained, according to Schroeter (Ber. 63, (1930) 1316) when tetrahydronaphthalone oxime is converted to α-naphthylamine. The oxime is reacted with acetic anhydride, while passing HCL gas through, and 56% of theory of α-naphthylamine hydrochloride are obtained here. Hardy and Ward (J. chem. Soc. 1956, 1979-81) obtained yields of a similar level in the conversion of nitrotetrahydronaphthalone oxime to nitronaphthylamine (38-45% of theory).

Concentrated sulfuric acid, 20% strength hydrochloric acid, polyphosphoric acid, acetic anhydride and acetyl chloride are described in the literature as "water-eliminating agents". The processes outlined above cannot be used for an economical, large-scale manufacture of aromatic amines because, inter alia, the necessary treatment of effluents also entails high costs.

It has now been found that the yields of aromatic amines can be considerably increased if the oxime hydrochlorides are employed in place of the free oximes and if at least three mols of acetic anhydride per mol of oxime hydrochloride are used. Thus, symmetrical m-xylidine is obtained from 3,5-dimethylcyclohexenone oxime hydrochloride and acetic anhydride in a yield of 86% of theory, whilst only about 25% of the base is formed when the pure oxime is used.

It is very surprising that this modification of the reaction which has been known for a long time, results in such an increase in yield.

The invention thus relates to a process for the manufacture of aromatic amines from the corresponding cyclohex-2-en-1-one oximes by reacting the oxime hydrochlorides with at least three mols of acetic anhydride per mol of hydrochloride.

Since at least a part of the hydrochloric acid reacts with the acetic anhydride while forming acetyl chloride in addition to the first mol of acetic anhydride necessary for eliminating the one mol of water and to the second mol of acetic anhydride necessary for acetylating the amino group a third mol of acetic anhydride is applied in order to obtain good yields. Preferred are 3 to 4 mols, especially 3.4 to 3.7 mols of acetic anhydride per mol of oxime hydrochloride.

Possible starting materials are all the cyclohex-2-en-1-one oximes in which any substituents which may be present are stable under the reaction conditions and do not react with the water-eliminating agent in an undesirable manner. Of course, the substituents on the cyclohexenone system must permit an aromatisation. Preferred cyclohex-2-en-1-one oximes are substituted by lower alkyl radicals, by phenyl radicals which are unsubstituted or substituted by inert substituents.

Substituents which are stable and inert under the reaction conditions are, in particular, lower alkyl groups, lower alkoxy groups, nitro groups, trifluoromethyl groups or carbamoyl and sulfamoyl groups which may be substituted on the nitrogen by lower alkyl groups, as well as halogen atoms, in particular chlorine atoms.

This increase in yield makes it possible to manufacture, in an economical manner, aromatic amines which are accessible only with difficulty by other routes. Due to the high yields, there are also no significant problems in working-up.

Advantageously, the oxime hydrochloride is introduced continuously or batchwise into acetic anhydride. The course of the reaction is strongly exothermic. If the acetic anhydride is preheated, the reaction can readily be controlled by the rate of introduction of the oxime hydrochloride. The oxime hydrochloride can be introduced either in the solid form or dissolved in a solvent. Glacial acetic acid is a particularly suitable solvent. It is also possible to prepare the oxime hydrochloride in situ by reacting the α,β-unsaturated cycloaliphatic ketoximes in the solvent with hydrogen chloride gas.

When forming the hydrochloride in situ while the acetic anhydride is already present care must be taken that the hydrochloride is formed before a substantial reaction with the acetic anhydride takes place. Since the formation of the hydrochloride occurs rapidly even in the cold no difficulties are encountered when introducing hydrogen chloride gas into a cold solution of the oxime in glacial acetic acid even when an excess of acetic anhydride is present.

When reacting highly reactive oxime hydrochlorides, e.g. of cyclohex-2-en-1-one, no heating of the reaction mixture is necessary. Thus, generally the reaction can be carried out between 0° C. and 200° C.; a temperature between 20° C. and 140° C., especially 80° C. to 140° C., is especially suitable. The reaction can be carried out under reflux or the heat of reaction can be utilized for distilling off the solvents or the acetic acid formed. If the liquid reaction products and excess acetic anhydride are distilled off after the reaction has ended, the acetamino compound can be isolated as an intermediate product. In general, however, the latter is immediately processed further to give the free amine.

In some cases it can be advantageous to carry out the reaction in the presence of hydrogen chloride. In that case, however, it must be noted that the metering of the latter must be matched to the particular oxime hydrochloride.

The amines manufactured by the process according to the invention are valuable intermediate products, for example for the manufacture of colorants.

In the Examples which follow, percentage data are by weight.

EXAMPLE 1

175 g of 3,5-dimethylcyclohex-2-en-1-one oxime hydrochloride are slowly introduced into 375 g of warm acetic anhydride at 80° C. During this procedure, the temperature rises up to the boiling point of the mixture. When all the oxime hydrochloride has been introduced, the acetic acid and the excess acetic anhydride are distilled off completely in a waterpump vacuum, 350 ml of water and 340 g of 31% strength hydrochloric acid are added to the residue and the mixture is boiled under reflux for 2 hours. After the dark-colored solution has been clarified, the pH is adjusted to at least 10 with about 564 g of 33% strength sodium hydroxide solution and the aqueous phase is separated at room temperature from the symmetrical m-xylidine which has separated out. The aqueous phase is extracted.

This gives 104 g (86% of theory) of crude m-xylidine of boiling point 70°–72° C./0.5 mm Hg.

EXAMPLE 2

125 g of 3-methylcyclohex-2-en-1-one oxime (1 mole) are dissolved in 250 g of acetic acid and 38 g of hydrogen chloride gas are passed into the solution. A thick, white, readily stirrable suspension is formed, and this is warmed to 80° C. in order to dissolve the 3-methylcyclohexenone oxime hydrochloride which has formed. This solution is added to 350 g of acetic anhydride room temperature and the mixture is then gradually warmed to the boiling point of the mixture. The further procedure is as indicated in Example 1. This gives 87 g of m-toluidine corresponding to 81% of the theoretical yield; boiling point 203° C.

I claim:

1. In a process for preparing an aromatic amine from the corresponding cyclohex-2-en-1-one oxime by treating it with agents capable of splitting off water the improvement comprising reacting the hydrochloride of said oxime with at least three mols of acetic anhydride per mol of oxime hydrochloride.

2. A process as claimed in claim 1, wherein the oxime hydrochloride is dissolved in a solvent.

3. A process as claimed in claim 1, wherein the cyclohexenone oxime hydrochloride derives from cyclohex-2-en-1-one substituted by lower alkyl, phenyl, lower alkyl-phenyl, lower alkoxy-phenyl, nitrophenyl, trifluoromethyl-phenyl, carbamoyl-phenyl, N-lower alkyl carbamoyl-phenyl, sulfamoyl-phenyl, N-lower alkyl sulfamoyl phenyl or chlorophenyl.

4. A process as claimed in claim 1, wherein the cyclohexenone oxime hydrochloride derives from 3,5-dimethyl-cyclohex-2-en-1-one or 3-methyl-cyclohex-2-en-1-one.

5. A process as claimed in claim 1, wherein said hydrochloride is reacted at 0° to 200° C.

6. A process as claimed in claim 5, wherein the temperature is 20° to 140° C.

7. A process as claimed in claim 5, wherein the temperature is 80° to 140° C.

8. A process as claimed in claim 1, wherein 3 to 4 mols of acetic anhydride are reacted.

9. A process as claimed in claim 1, wherein 3.4 to 3.7 mols of acetic anhydride are reacted.

* * * * *